(12) United States Patent
Castel et al.

(10) Patent No.: US 8,491,212 B2
(45) Date of Patent: Jul. 23, 2013

(54) MULTI-FUNCTIONAL APPLICATOR

(75) Inventors: John C. Castel, Reno, NV (US); R. Patrick Abergel, Santa Monica, CA (US)

(73) Assignee: Laboratoire Naturel Paris, LLC, Reno, NV (US)

( * ) Notice: Subject to any disclaimer, the term of this patent is extended or adjusted under 35 U.S.C. 154(b) by 582 days.

(21) Appl. No.: 12/049,800

(22) Filed: Mar. 17, 2008

(65) Prior Publication Data

US 2009/0232580 A1 Sep. 17, 2009

(51) Int. Cl.
*B43K 5/14* (2006.01)

(52) U.S. Cl.
USPC .......................... 401/133; 401/132

(58) Field of Classification Search
USPC ........... 401/132–135, 183; 604/1, 3; 206/222, 206/219
See application file for complete search history.

(56) References Cited

U.S. PATENT DOCUMENTS

| | | | |
|---|---|---|---|
| 1,332,985 A * | 3/1920 | Jarrett | 206/222 |
| 3,294,227 A | 12/1966 | Schneider et al. | |
| 3,608,709 A | 9/1971 | Pike | |
| 3,756,389 A | 9/1973 | Firth | |
| 3,757,782 A * | 9/1973 | Aiken | 604/3 |
| 3,759,259 A | 9/1973 | Truhan | |
| 3,958,571 A | 5/1976 | Bennington | |
| 4,740,194 A * | 4/1988 | Barabino et al. | 401/132 |
| 4,776,836 A * | 10/1988 | Stanley | 604/3 |
| 4,778,457 A | 10/1988 | York | |
| 4,784,506 A | 11/1988 | Koreska et al. | |
| 4,799,815 A | 1/1989 | Barabino et al. | |
| 4,812,067 A | 3/1989 | Brown et al. | |
| 4,863,422 A * | 9/1989 | Stanley | 604/3 |
| 4,983,382 A * | 1/1991 | Wilmott et al. | 424/62 |
| 5,140,043 A | 8/1992 | Darr et al. | |
| 5,287,961 A | 2/1994 | Herran | |
| 5,325,273 A * | 6/1994 | Kuo | 206/219 |
| 5,458,244 A | 10/1995 | Emori | |
| 5,490,736 A | 2/1996 | Haber et al. | |
| 5,558,874 A | 9/1996 | Haber et al. | |
| 5,568,988 A | 10/1996 | Knox et al. | |
| 5,616,337 A | 4/1997 | Kasianovitz et al. | |
| 5,804,213 A | 9/1998 | Rolf | |
| 5,902,591 A | 5/1999 | Herstein | |
| 6,007,264 A * | 12/1999 | Koptis | 401/132 |
| 6,036,887 A | 3/2000 | Guerin et al. | |
| 6,299,798 B1 | 10/2001 | Guerin et al. | |
| 6,361,783 B2 | 3/2002 | Moaddel et al. | |

(Continued)

FOREIGN PATENT DOCUMENTS

| DE | 29 20 213 | 11/1980 |
|---|---|---|
| EP | 0 553 534 | 8/1992 |

(Continued)

OTHER PUBLICATIONS

International Search Report and Written Opinion dated Jan. 26, 2010; 8 pages.

*Primary Examiner* — David Walczak
*Assistant Examiner* — Jennifer C Chiang
(74) *Attorney, Agent, or Firm* — Stinson Morrison Hecker LLP

(57) ABSTRACT

A multifunctional multi-compartment applicator for the stable storage of solid ascorbic acid and topical application of ascorbic acid in solution to the skin, the applicator having an absorbent end and an abrasive end.

16 Claims, 7 Drawing Sheets

U.S. PATENT DOCUMENTS

| | | | |
|---|---|---|---|
| 6,503,013 B2 | 1/2003 | Strauss | |
| 6,547,468 B2 | 4/2003 | Gruenbacher et al. | |
| 6,595,940 B1 | 7/2003 | D'Alessio et al. | |
| 6,695,515 B1 | 2/2004 | Fleury | |
| 6,789,971 B2 * | 9/2004 | Tsaur | 401/132 |
| 6,811,338 B1 | 11/2004 | Manske, Jr. et al. | |
| 6,902,335 B2 | 6/2005 | Bergey et al. | |
| 6,945,402 B1 | 9/2005 | Gueret | |
| 6,960,041 B2 * | 11/2005 | Tsaur | 401/133 |
| 7,025,521 B2 * | 4/2006 | Tsaur | 401/132 |
| 7,186,046 B2 * | 3/2007 | Kauffmann et al. | 401/132 |
| 2002/0053576 A1 | 5/2002 | Manne | |
| 2006/0239757 A1 * | 10/2006 | Giniger | 401/132 |
| 2007/0119862 A1 | 5/2007 | Backes et al. | |
| 2007/0190173 A1 | 8/2007 | Blotsky et al. | |
| 2007/0223988 A1 | 9/2007 | Gruenbacher et al. | |
| 2008/0003052 A1 | 1/2008 | Lee et al. | |

FOREIGN PATENT DOCUMENTS

| | | |
|---|---|---|
| WO | WO 97/06076 | 2/1997 |
| WO | WO 98/34581 | 8/1998 |
| WO | WO 00/09016 | 2/2000 |
| WO | WO 00/26280 | 5/2000 |
| WO | WO 01/17390 | 3/2001 |

* cited by examiner

MULTI-FUNCTIONAL APPLICATOR

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

1. Field of the Invention

The present invention relates to an applicator and method for the topical delivery of Vitamin C (ascorbic acid) to the skin. More particularly, the present invention relates to a transdermal drug delivery device and delivery method for Vitamin C (ascorbic acid) comprising a combination of skin preparation using abrasion and the dispensing of ascorbic acid through an applicator device containing a dry powder form of ascorbic acid which is placed in solution or other suitable carrier just prior to use, thus maintaining maximum efficacy of the ascorbic acid when applied to the skin surface.

2. Description of Related Art

The present invention relates to a device for the topical or transdermal delivery of Vitamin C (ascorbic acid) and its pharmaceutically acceptable salts and esters. Ascorbic acid has many known biological functions from enzymatic co-factor to "sparing" agent against Vitamin E depletion. The latter function may partly account for its "anti-oxidant" status. Additionally, at higher concentrations, ascorbic acid is known to react with both superoxide and hydroxyl radicals. Superoxide and the subsequently generated hydrogen peroxide and hydroxyl radical are oxygen-containing free radicals now known to be generated in vivo under a variety of normal and pathological conditions. Quite simply, these radicals have been implicated as causative agents for everything from sunburn to aging. These radicals destroy lipid membranes, breakdown DNA, inactivate enzymes, and so forth.

Ascorbic acid is also thought to be involved in wound healing. The process of wound healing generally encompasses three phases during which the injured tissue is repaired, regenerated, and new tissue is reorganized into a scar. These three phases are classified as: (a) an inflammation phase which begins from about day 0 to 3 days, (b) a cellular proliferation phase from about 3 to 12 days, and (c) a remodeling phase from about 3 days to about 6 months. In all three phases, antioxidants, such as Vitamin C, play a vital role in the healing process.

In the inflammation phase, inflammatory cells, mostly neutrophils, enter the site of the wound followed by lymphocytes, monocytes, and later macrophages. The neutrophils that are stimulated begin to release proteases and reactive oxygen species into the surrounding medium with potential adverse effects on both the adjacent tissues and the invading microorganisms.

The proliferative phase consists of laying down new granulation tissue, and the formation of new blood vessels in the injured area. The fibroblasts, endothelial cells, and epithelial cells migrate in the wound site. These fibroblasts produce the collagen that is necessary for wound repair. Ascorbic acid is crucial in the formation of collagen. Several studies have demonstrated that ascorbic acid was capable of overcoming the reduced proliferative capacity of elderly dermal fibroblasts, as well as increasing collagen synthesis in elderly cells by similar degrees as in newborn cells even though the basal levels of collagen synthesis are age dependent. A decrease of ascorbic acid at the injury area will decrease the rate of wound healing.

In reepithelialization, epithelial cells migrate from the free edges of the tissue across the wound. This event is succeeded by the proliferation of epithelial cells at the periphery of the wound. Research has also shown that reepithelialization is enhanced by the presence of occlusive wound dressings which maintain a moisture harrier.

The final phase of wound healing, which is remodeling, is affected by both the replacement of granulation tissue with collagen and elastin fibers and the devascularization of the granulation tissue. Recent studies have shown that topical application of antioxidants reduces scarring and normalizes blood coagulation during therapy.

L-Ascorbic acid is chemically defined as an alpha-ketolactone and containing an acid-ionizable hydrogen in water (pK=4.2). Ascorbic acid is also a moderately strong reductant. These properties, which lead to instability in the ascorbic acid structure, are well known and have been burdensome to pharmacologists when attempting to formulate active ascorbic acid solutions. Thus, at higher pHs values, the ascorbic acid increasingly becomes the notoriously unstable ascorbate anion. This instability may be due to several causes not restricted to stereochemical strain, oxidative degradation, and degradation due to water attack.

For these reasons, among others, scientists working in the field have had difficulty in formulating stable solutions of ascorbic acid which would be useful for cosmetic or dermatological needs. Nevertheless, because of the many beneficial pharmaceutical effects attributed to ascorbic acid, numerous attempts have been made to overcome these difficulties.

BRIEF SUMMARY OF THE INVENTION

The present invention is directed to a novel applicator for the topical or transdermal delivery of ascorbic acid and its pharmaceutically acceptable salts and esters to a subject in need thereof. The applicator is easily transportable, suitable for single use, and inexpensive to manufacture. The device is capable of storing ascorbic acid and its pharmaceutically acceptable salts and esters in a solid stable powder form prior to delivery in solution or other carrier to the skin. Further, device incorporates the use of mechanical abrasion of the skin surface followed by the application of topical ascorbic acid and its pharmaceutically acceptable salts and esters as part of the wound healing process.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

DETAILED DESCRIPTION OF PREFERRED EMBODIMENT

Figure 1:
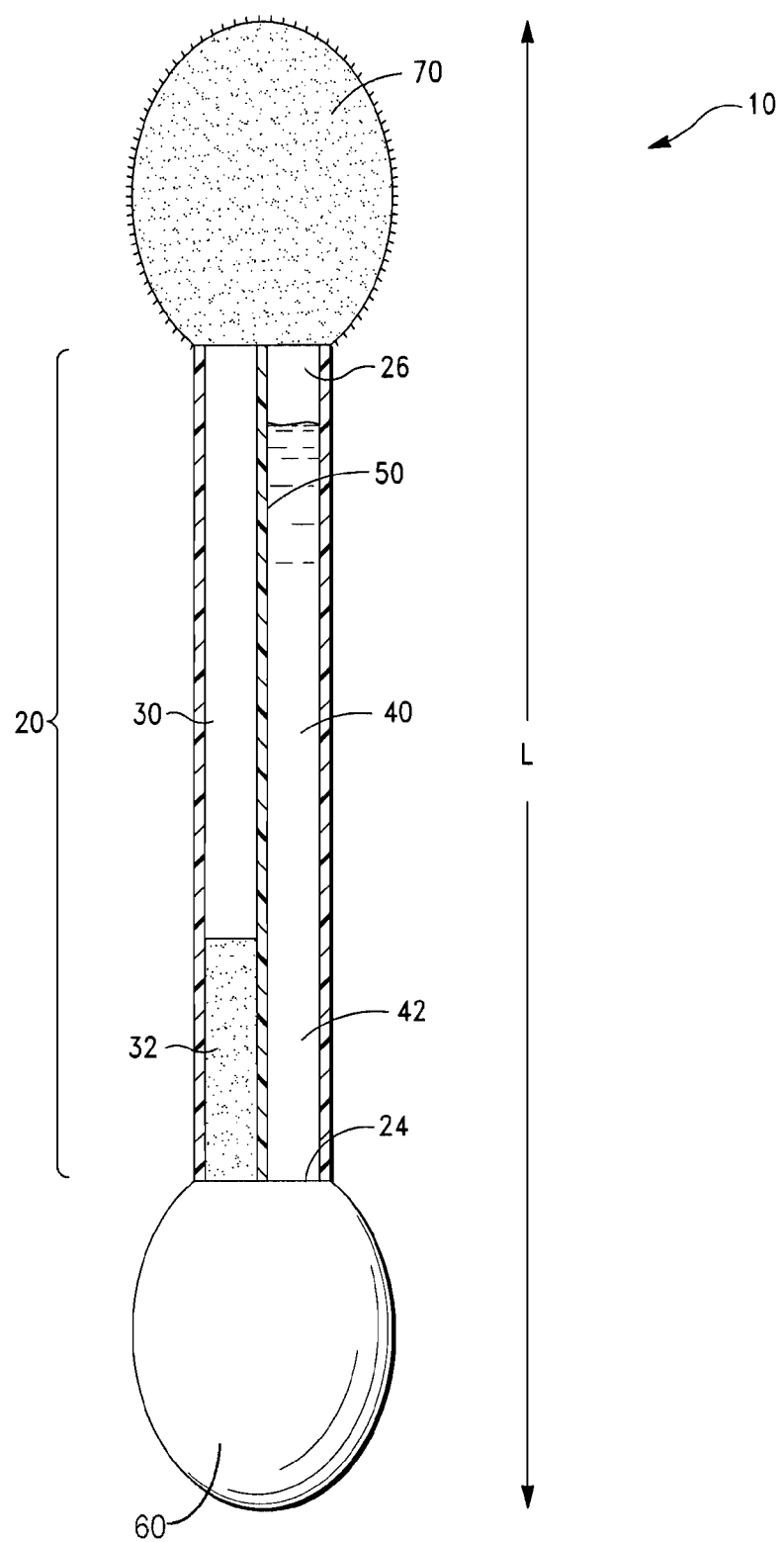
FIG. 1 is a perspective view of the applicator device of the present invention having two compartments separated by a divider for holding a powdered ascorbic acid (or its pharmaceutically acceptable salts and esters) composition in the first compartment and a carrier system in the second compartment.

The present invention is directed to device 10 for applying a therapeutic composition comprising ascorbic acid or its pharmaceutically acceptable salts and esters to the skin. As shown in FIG. 1, the device comprises an elongated hollow body 20 having at least two proximal compartments 30, 40 separated by a divider 50. A solid vitamin-containing composition 32 comprising ascorbic acid or its pharmaceutically acceptable salts and esters is housed in the first compartment 30. A pharmaceutically acceptable carrier system 42, such as water and/or ethyl alcohol, is housed in the second compartment 40.

The vitamin-containing composition 32 comprising ascorbic acid or its pharmaceutically acceptable salts and esters in the first compartment 30 contains a therapeutically effective amount of ascorbic acid or its pharmaceutically acceptable salts and esters. A therapeutically effective amount of antioxidant is that amount of antioxidant necessary for the inventive composition to prevent and reduce injury to mammalian cells or increase the resuscitation rate of injured mammalian cells. The exact amount of antioxidant is a matter of preference subject to such factors as the type of condition being treated as well as the other ingredients or excipients in the composition. Typically, the vitamin-containing composition comprises about 200 to 800 milligrams of ascorbic acid, or its pharmaceutically acceptable salts or esters in the form of a crystalline powder. However, it is to be expressly understood that the ascorbic acid could also take the form of a dry medication wafer or other solid form, rather than a powder.

The solid vitamin-containing composition 32 may contain other therapeutic agents. Preferred therapeutics include collagen type I, alpha-tocopherol (vitamin E), and particulate starch hydrolysate that are applied on wounds to promote the formation and growth of healthy granulation tissue. In addition to ascorbic acid, the therapeutic composition may contain additional antioxidants. In general, antioxidants are substances which inhibit oxidation or suppress reactions promoted by oxygen or peroxides. Antioxidants, especially lipid-soluble antioxidants, can be absorbed into the cellular membrane to neutralize oxygen radicals and thereby protect the membrane. The antioxidants useful in the present invention are preferably selected from the group consisting of all forms of vitamin A (retinol), all forms of vitamin $A_2$ (3,4-didehydroretinol), all forms of carotene such as alpha-carotene, beta-carotene, gamma-carotene, delta-carotene, all forms of vitamin C (D-ascorbic acid, L-ascorbic acid), all forms of tocopherol such as vitamin E (alpha-tocopherol, 3,4-dihydro-2,5,7,8-tetramethyl-2-(4,8,12-trimethyltri-decyl)-2H-1-benzopyran-6-ol), beta-tocopherol, gamma-tocopherol, delta-tocopherol, tocoquinone, tocotrienol, and vitamin E esters which readily undergo hydrolysis to vitamin E such as vitamin E acetate and vitamin E succinate, and pharmaceutically acceptable vitamin E salts such as vitamin E phosphate, prodrugs of vitamin A, carotene, and vitamin E, pharmaceutically acceptable salts of vitamin A, carotene, and vitamin E, and the like, and mixtures thereof. Preferably, the additional antioxidant is selected from the group of lipid-soluble antioxidants consisting of vitamin A, beta-carotene, vitamin E, vitamin E acetate, and mixtures thereof.

The pharmaceutically acceptable carrier system 42 in the second compartment 40 is preferably a liquid, cream, lotion, gel, or paste. The rheological properties of the carrier system 42 are such that the carrier system 42 can be readily mixed with the solid vitamin-containing composition 32, including by manually moving the carrier from one compartment to the other. In one embodiment, the carrier system preferably comprises water. The carrier system in the second compartment may optionally comprise one or more organic solvents miscible with water. There are many mono, di, or polyhydric liquids suitable for this purpose including, for example, the alcohols, glycols, and polyols. Without limitation, one or more of the following organic solvents may be employed ethanol, N-propanol, isopropyl alcohol, methanol, propylene glycol, butylene glycol, hexylene glycol, glycerine, sorbitol (polyol), di-propylene glycol, and polypropylene glycol. The organic solvent may comprise up to about 90% by weight of the carrier system. See generally Wilmott et al., U.S. Pat. No. 4,983,382, which is incorporated by reference. In addition, other therapeutic agents, chelators, pH regulators, or carriers, may be dissolved, dispersed, or emulsified in the carrier system. See generally Darr et al., U.S. Pat. No. 5,140,143, which is incorporated by reference. Exemplary therapeutics are discussed above and include without limitation, growth agents, growth factors or hormones, growth inhibitors, serums, treatment material, cleaners, vitamins, exfoliators, lubricants, or other substances that can be used to treat a patient's skin.

In order to avoid obtaining a therapeutic composition which is too acidic (i.e., a pH less than 3.5) after introducing the ascorbic acid or its pharmaceutically acceptable salts and esters, it is preferable to add to the carrier system one or more pH-regulating agents. Examples of such agents include sodium citrate or sodium acetate buffer. The quantity of buffer is a function of the quantity of ascorbic acid used and the desired final pH; the latter is typically from 3.0 to 6, more preferably from 3.8 to 4.5 but including all values and all ranges there between.

Figure 5:
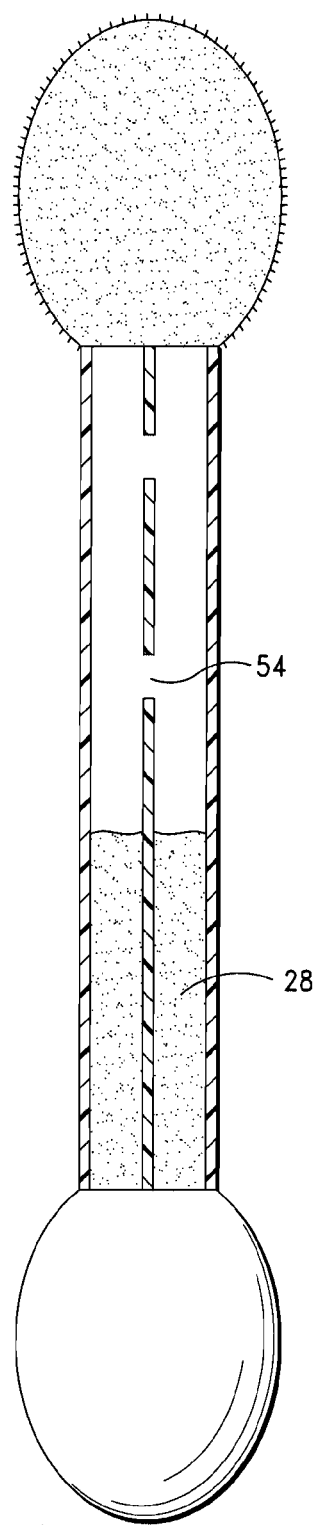
FIG. 5 is a perspective view of the applicator device in which the contents of the two compartments have been mixed together after one or more openings have been made in the longitudinal divider.

As discussed more fully below, one or more openings 54 are formed in the divider 50. The carrier system 42 in the proximal second compartment is then introduced to and mixed with vitamin-containing composition 32 comprising ascorbic acid or its pharmaceutically acceptable salts and esters in order to form an ascorbic acid carrier composition 28 just prior to treatment (FIG. 5). Preferably, the ascorbic acid carrier composition comprises about 2 wt. % and 35 wt. % ascorbic acid or its pharmaceutically acceptable salts and esters, and most preferably between about and 10 wt. % to 25 wt. % ascorbic acid or its pharmaccutically acceptable salts and esters, although other concentrations may be used based on the desired therapeutic effect.

Prior to use, the vitamin-containing composition 32 comprising ascorbic acid or its pharmaceutically acceptable salts and esters is separated from the carrier system 42 with a divider 50. The divider is preferably disposed along the longitudinal axis L of the elongated hollow body. The divider 50 contains one or more means for forming an opening therein and permitting the contents of the first compartment and second compartment to mix.

Figure 2A:
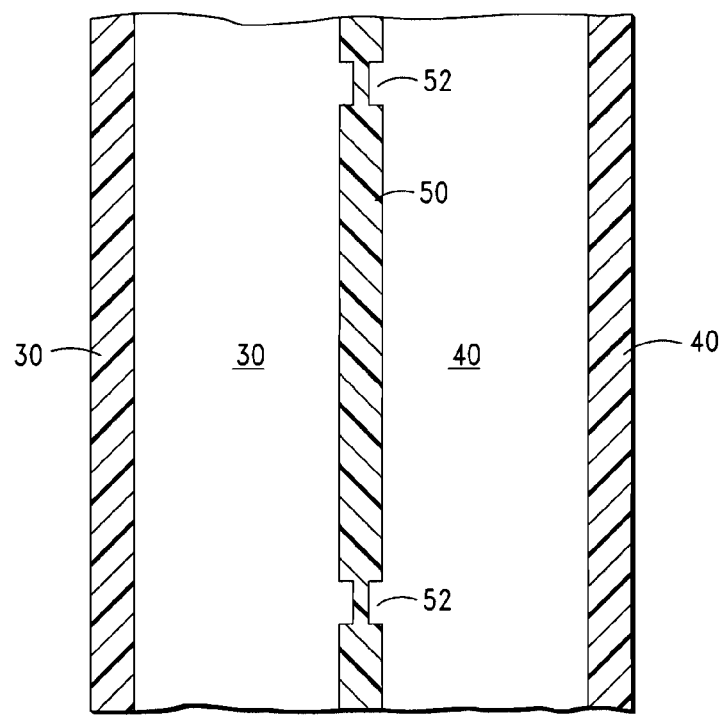
FIG. 2A is a cut-out of a first embodiment of a portion the elongated body of the application device. The longitudinal divider contains one or more zones of weakness suitable for creating openings in the divider.

In one embodiment, as shown in FIG. 2A, the divider 50 comprises a membrane having one or more zones of weakness 52, such as a declivity or score line. Thus, when the hollow body is bent, flexed, or compressed along the zone of weakness 52, an opening 54 is created in the divider, permitting the contents of the first compartment 30 and the second compartment 40 to mix. Mixing may be facilitated by the user merely by shaking or moving the device.

The zones of weakness 52 may be readily visualized by the user when the elongated hollow body is sufficiently translucent to visible light. The elongated hollow body may optionally have one or more markings corresponding to the zones of weakness 52 so that the user may visualize where the bending, flexing, or compressing forces should be localized in order to create the opening in the divider.

Figure 3A:
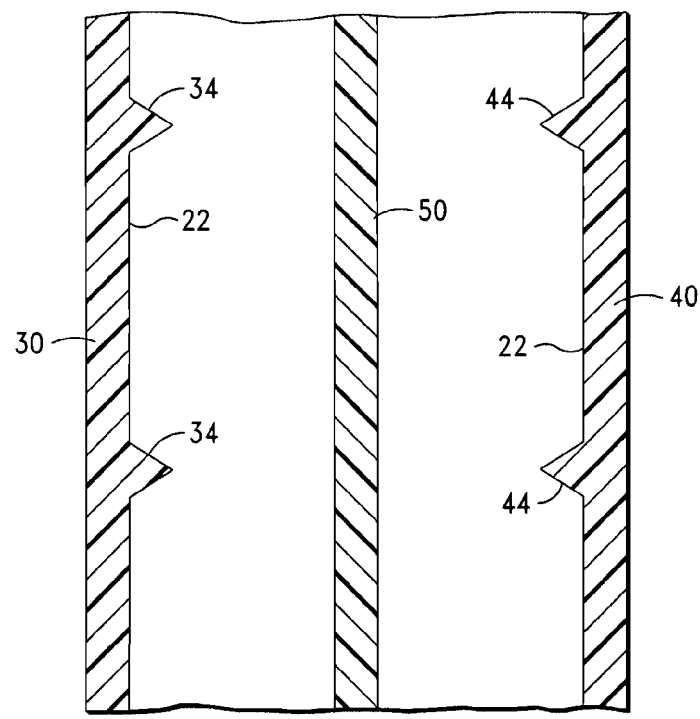
FIG. 3A is a cut-out of a second embodiment of a portion the elongated body. The elongated hollow body contains one or more puncture tips suitable for creating openings in the longitudinal divider.
Figure 3B:
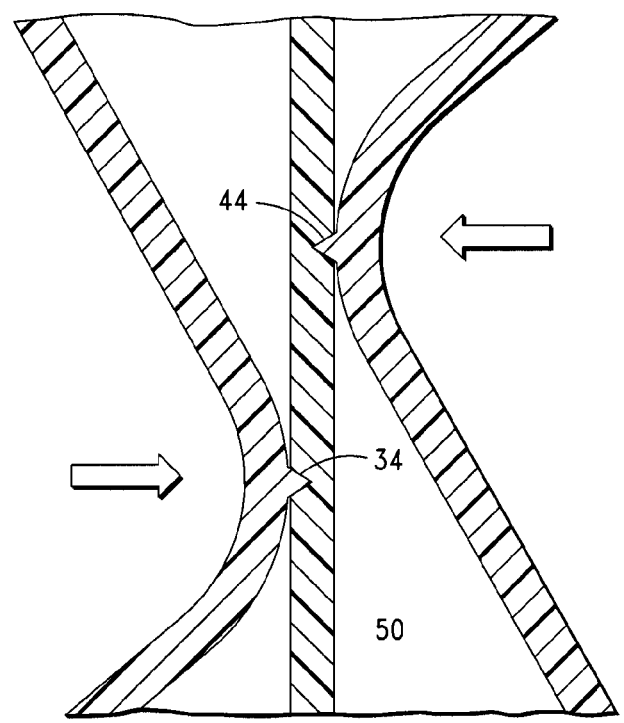
FIG. 3B illustrates how the elongated hollow body may be flexed or bent so that the puncture tips engage and puncture the divider.
Figure 3C:
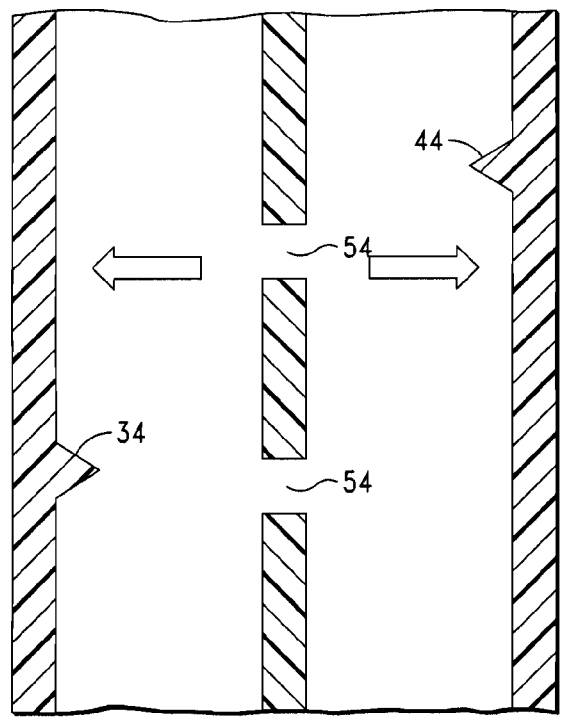
FIG. 3C illustrates the resulting openings in the divider.

In another embodiment, as shown in FIGS. 3A-3C, one or more puncture tips 34, 44 are provide along inner surface 22 of the hollow body 20. When a compressive, bending or flexing force is applied against the puncture tips 34, 44, the tips puncturely engage the divider 50 (FIG. 3B), and form an opening 54 therein (FIG. 3C), permitting the contents of the first compartment and the second compartment to mix.

The puncture tips 34, 44 may be readily visualized by the user when the elongated hollow body is sufficiently translucent. The elongated hollow body may optionally have one or more markings corresponding to the puncture tips 34, 44 so that the user may visualize where the bending, compression, or twisting forces should be localized in order to create the opening in the divider.

The hollow body 20 is preferably manufactured from a gas and liquid impermeable, heat sealable material that is suitable for thermal bonding or sonic welding. This material is both flexible and optically translucent to visible light so that the user will be able to manually manipulate the contents of the compartments to and visualize mixing thereof. An exemplary material is commercially available Mylar-polyethylene barrier layer material. Other suitable materials include high-density polyethylene, polypropylene, polystyrene, polyvinylchloride, and the like. Preferably, the material used to form the hollow body 20 is impermeable to ultraviolet light in order to reduce the potential for oxidation, photoactivation or photoreduction of the contents. If the hollow body 20 is permeable to ultraviolet light, the device is preferably stored in the dark prior to use.

Figure 4A:
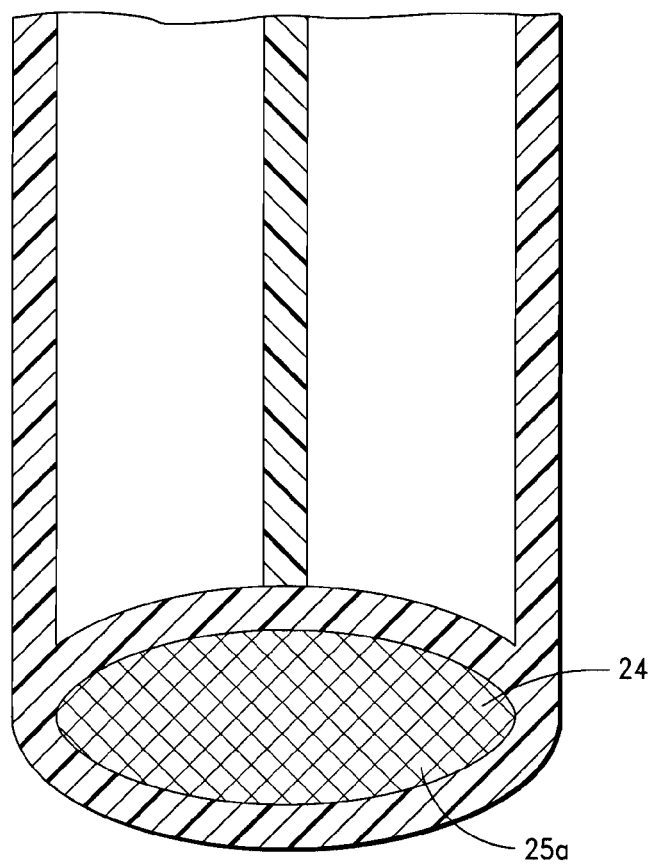
FIG. 4A is a cut-out of a first embodiment of the frangible seal covering the end of the hollow body. The absorbent material is removed for illustration only.
Figure 4B:
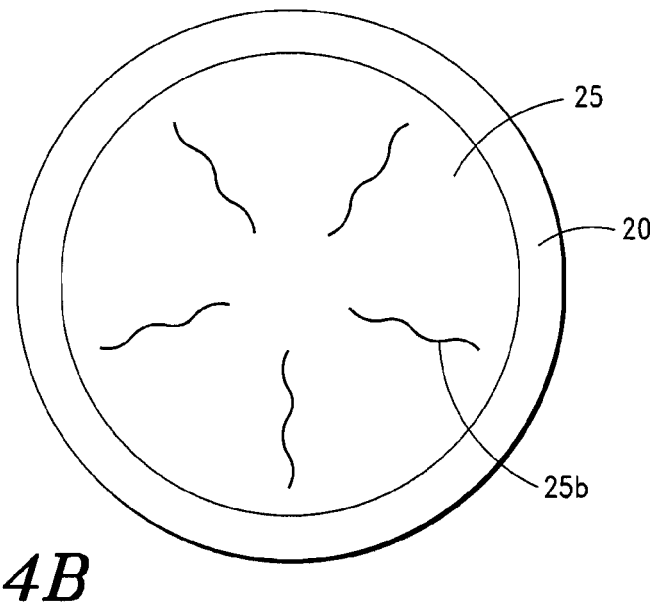
FIG. 4B is a top view of a second embodiment of the frangible seal covering the end of the hollow body. The absorbent material is removed for illustration only.

The hollow body 20 has an opening at a first end 24. A frangible seal 25 closes the opening to retain the contents housed in the hollow body. In one embodiment, the frangible seal comprises a thin membrane 25a (FIG. 4A). For example, thin films of plastic or aluminum foil can be heat sealed to the hollow body to cover the opening in the first end 24. Upon bending the walls of the hollow body at or near the frangible seal 25, the seal is broken. In another embodiment (FIG. 4B), the frangible seal comprises a cover having a zone of weakness. For example, the cover may have one or more score lines 25b so that when a compression force is applied near the cover, the score lines are broken, permitting fluid, cream, lotion, gel, or paste to pass therethrough. Other exemplary frangible seals are disclosed in Truhan, U.S. Pat. No. 3,759,259, which is incorporated by reference.

An absorbent material 60 is positioned at the first end 24 of the hollow body 20. The absorbent material is of a known type, including but not limited to cotton fibers or synthetic fibers, such as plastic fibers, or a semi-porous material, such as a sponge. When the frangible seal 25 is broken, the contents of the hollow body 32, 42 that have been mixed together to form a ascorbic acid carrier composition 28 are released into the absorbent material 60, and ultimately applied to the user's skin.

An abrasive material 70 is positioned at the second end 26 of the hollow body. The abrasive material 70 is such that the rubbing against the skin will cause significant exfoliation. Abrasion of the outer layer or epidermis (stratum corneum) of the skin is desirable to smooth or blend scars, blemishes, or other skin conditions that may be caused by, for example, acne, sun exposure, and aging. In addition, abrasion of the skin also facilitates the transdermal delivery of the ascorbic acid carrier composition 28 to the skin. The abrasion also triggers the degranulation of mast cells to trigger the inflammatory phase of healing.

A commercially available uniform, lofty, open, non-woven, three-dimensional, lightweight abrasive web material is available from the Minnesota Mining and Manufacturing (3M) Company and is sold for commercial and industrial applications under the trade name Scotch-Brite, as described in Hoover et al., U.S. Pat. No. 2,958,593, and Klecker et al., U.S. Pat. No. 4,078,340, and Heyer et al., U.S. Pat. No. 5,363,604, the entire disclosures of which are incorporated herein by reference. Specific reference is made to the photograph of FIG. 1 in U.S. Pat. No. 2,958,593, illustrating the globules of binder carrying abrasive particles and showing the open, lofty structure defining the voids between the filaments in the structure which the applicant has discovered is so well suited to gently abrading and exfoliating the epidermis and accumulating the detritus from the horny corneal layer of the over skin. Other exemplary abrasive materials include but are not limited to silica sand, aluminum oxide (corundum), pumice, rouge (iron oxide), feldspar, silicon carbide, boron carbide, cerium oxide, quartz, garnet, titanium dioxide, calcium carbonate, calcium phosphate, diatomaceous earth, perlite, kaolin, mica, tripoli, ridig polymeric materials, talc, vermiculite, water absorbent soft abrasives, and combinations thereof. An abrasive sandpaper be bonded to a sponge or other suitable material at second end 26 of the hollow body. The sandpaper may have a larger or smaller grain size depending upon the degree of exfoliation desired.

To activate and use the applicator 10, the user first squeezes or bends the hollow body 20 so as to apply a compressive or bending force against the divider 50, thereby creating one or more openings 54 in the divider. The contents of the first compartment 30 and second compartment 40 are then mixed together. Typically, the carrier system 42 readily flows into the first compartment 30 through the openings 54. The vitamin-containing composition 32 comprising ascorbic acid or its pharmaceutically acceptable salts and esters 32 is hydrated to form a ascorbic acid carrier composition 28. The ascorbic acid carrier composition 28 may be transferred back and forth between the compartments 30, 40 by the user to ensure that the entire volume of the carrier system 42 has been mixed with the vitamin-containing composition 32 comprising ascorbic acid or its pharmaceutically acceptable salts and esters.

Once the contents of the first compartment and second compartment have been mixed (e.g., either by gravity, shaking, capillary action, or otherwise) to form the ascorbic acid carrier composition 28, the frangible seal 25 is broken, permitting the ascorbic acid carrier composition 28 to be distributed to the absorbent material 60. Prior to application, however, the epidermis of the subject is abraded using the abrasive material 70 at the other end of the device 10. The abrading step may occur prior to, after, or during the step of mixing the contents of the compartments 30, 40. Preferably, the abrading step is performed within minutes (typically less than 5 minutes) prior to the application of the ascorbic acid carrier composition 28 to the skin.

Figure 6:
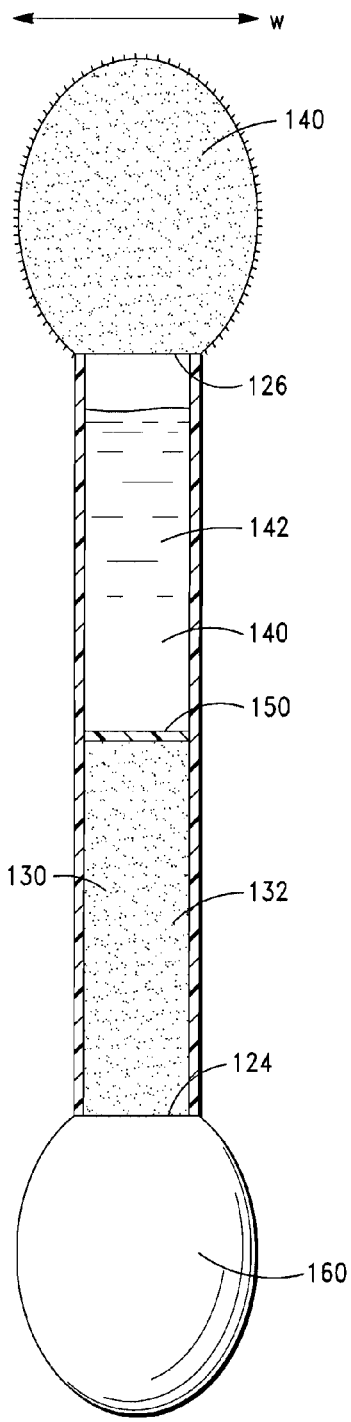
FIG. 6 is a perspective view of the applicator device wherein the divider is positioned in a transverse direction.
Figure 7A:
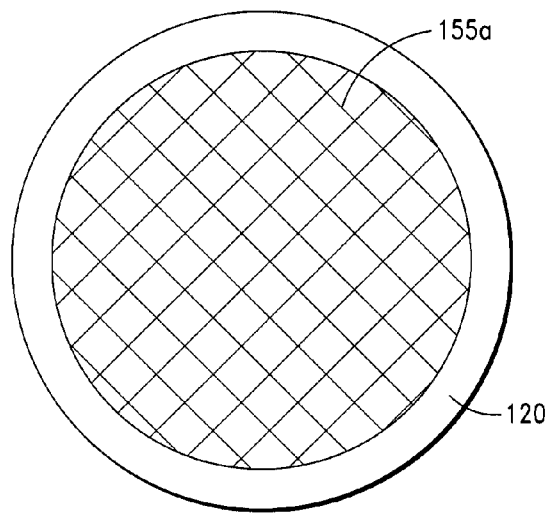
FIGS. 7A and 7B are cross-sections of two alternative transverse dividers illustrated in FIG. 6.
Figure 7B:
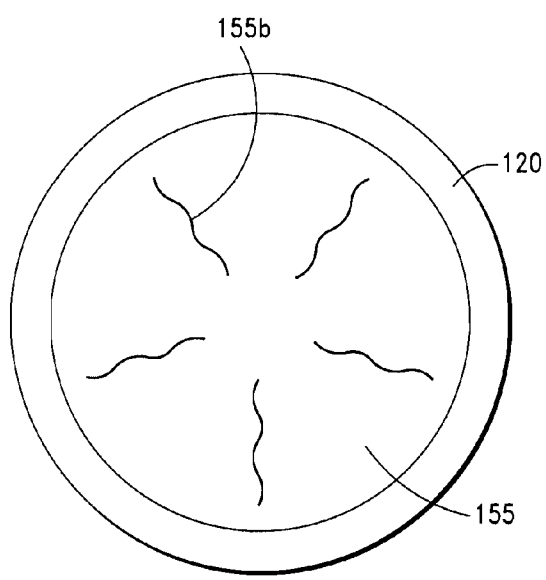

FIGS. 6, 7A, and 7B illustrate the transdermal drug delivery device 110 in accordance with a third embodiment of the present invention. In this embodiment, prior to use, the vitamin-containing composition 132 comprising ascorbic acid or its pharmaceutically acceptable salts and esters in the first compartment 130 is separated from the carrier system 142 in the second compartment 140 with a divider 150. In this embodiment, the divider is disposed along the transverse axis or width W of the elongated hollow body. The divider 150 contains one or more means for forming an opening therein and permitting the solid vitamin-containing composition 132 comprising ascorbic acid or its pharmaceutically acceptable salts and esters in the first compartment 130 and pharmaceutically acceptable carrier system 142 (e.g., water and ethanol) in the second compartment 140 to mix. As with the prior embodiments, the first end 124 of the hollow body 120 has an absorbent material 160 thereon, and the second end 126 has an abrasive material 170 thereon. Further, as with the prior embodiments, the first end 124 contains a frangible seal for permitting the contents of the hollow body 120 to flow therethrough to the absorbent material 160 to be ultimately applied to the user's skin.

Figure 8:
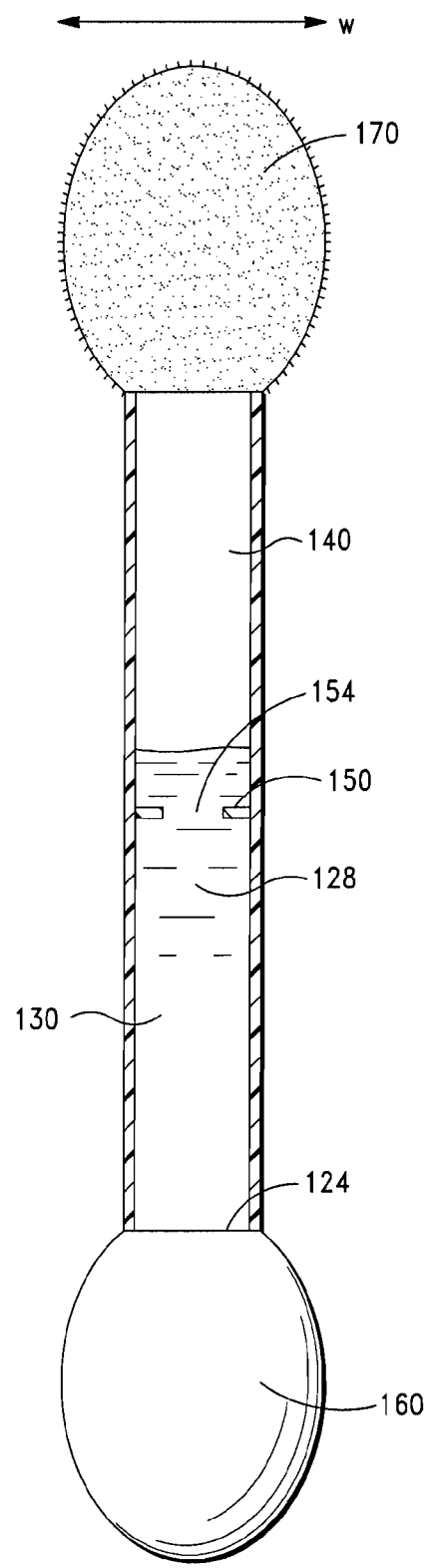
FIG. 8 is a perspective view of the applicator device of FIG. 6 in which the contents of the two compartments have been mixed together after one or more openings have been made in the transverse divider.

The transverse divider 150 preferably comprises a breakable seal 155 that separates the first compartment 130 from the second compartment 140. The breakable seal comprises a thin membrane 155a (FIG. 7A). For example, thin films of plastic or aluminum foil can be heat sealed to the hollow body. Upon bending, compressing, or twisting the walls of the hollow body at or near the breakable seal 155, the breakable seal is broken. In another embodiment (FIG. 7B), the breakable seal comprises a solid material having a zone of weakness. For example, the solid material may have one or more score lines 125b so that when a compression or other force is applied near the breakable seal, the score lines are broken, permitting the carrier system 142 to pass in an opening 154 therethrough. The contents of the hollow body 120 are then mixed together as generally shown in FIG. 8 to form a ascorbic acid carrier composition 128 comprising ascorbic acid or its pharmaceutically acceptable salts and esters.

The transdermal drug delivery device 10 is typically the size of a standard cotton three-inch swab applicator, but may any suitable size, such as an applicator about twice that size. In one aspect, the device is capable of holding about 1 to 10 ml of fluid, cream, lotion, gel, or paste. The device can be gripped and firmly controlled in a self-care procedure within a user's hand. The device is also preferably shaped in a fashion to provide easy handling and application by the individual or patient to the skin to be treated.

Although the hollow body 20 has been depicted as a hollow tube, it is understood that the invention contemplates the use of a hollow member having various types of cross-sectional configurations, i.e., polyganol cross-sections such as triangular, square, pentagonal, etc., as well as fluted sections. In addition, it is within the concept of this invention to provide an elongated hollow member divided into two or more longitudinal or transverse sections, each of which can contain separate distinct compositions which can mix and/or react together when they drain into the absorbent portion of the swab.

From the foregoing, it will be seen that this invention is one well adapted to attain all ends and objectives herein above set forth, together with the other advantages which are obvious and which are inherent to the invention. Since many possible embodiments may be made of the invention without departing from the scope thereof, it is to be understood that all matters herein set forth or shown in the accompanying drawings are to be interpreted as illustrative, and not in a limiting sense. While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

What is claimed and desired to be secured by Letters Patent is as follows:

1. A method for delivering ascorbic acid to the skin of a subject in need thereof comprising the steps of:
   providing a single-use, disposable applicator; said applicator having a hollow body having a first compartment containing a solid vitamin-containing composition comprising ascorbic acid or its pharmaceutically acceptable sales or esters, a second compartment containing a pharmaceutically acceptable carrier system; wherein said hollow body includes a single longitudinal divider between said first compartment containing said vitamin-containing composition and said second compartment containing said pharmaceutically acceptable carrier system; said applicator having a means for mixing said solid vitamin-containing composition and said pharmaceutically acceptable carrier system to form an ascorbic acid carrier composition inside said hollow body by creating one or more predetermined localized openings in said longitudinal divider; said mixing means comprising one or more zones of weakness in said longitudinal divider or one or more puncture tips extending from an inner surface of said hollow body that are capable of puncturely engaging said longitudinal divider;
   said applicator having an absorbent material positioned at a first end of said hollow body; and said applicator having an abrasive material positioned at a second end of said hollow body;
   abrading said skin using said abrasive material;
   mixing said solid vitamin-containing composition and said pharmaceutically acceptable carrier system together in said hollow body to form an ascorbic acid carrier composition;
   applying said ascorbic acid carrier composition to said abraded skin; and
   wherein said abrading step occurs before said mixing step.

2. The method of claim 1 wherein said divider has one or more zones of weakness; and wherein said mixing step comprises compressing, bending, or twisting said divider at said zone of weakness to form an opening in said divider.

3. The method of claim 1 wherein said mixing means comprises one or more puncture tips extending from an inner surface of said hollow body that are capable of puncturely engaging said divider, and wherein said mixing step comprises applying a compressing, bending, or twisting force against the puncture tips such that the tips puncturely engage said divider to form an opening in said divider.

4. The method of claim 1 wherein said providing step comprises providing said applicator in which said hollow body is impermeable to ultraviolet light.

5. The method of claim 1 wherein said providing step comprises providing said applicator in which said hollow body is translucent.

6. The method of claim 1 wherein said applying step comprises breaking a frangible seal at a terminal opening in said hollow body.

7. The method of claim 1 wherein applying step comprises applying said ascorbic acid carrier composition to wounded skin.

8. The method of claim 1 wherein said providing step comprises providing said ascorbic acid carrier composition having about 10 to 35 wt. % ascorbic acid.

9. The method of claim 1 wherein said providing step comprises providing said applicator in which said second compartment further contains one or more therapeutic agents, chelators, or pH regulators.

10. The method of claim 1 wherein said hollow body is impermeable to ultraviolet light.

11. The method of claim 1 wherein said wherein said mixing means comprises-one or more zones of weakness in said longitudinal divider.

12. The method of claim 1 wherein said mixing means comprises one or more puncture tips extending from an inner surface of said hollow body that are capable of puncturely engaging said longitudinal divider.

13. The method of claim 1 wherein said carrier system comprises water.

14. The method of claim 1 wherein said carrier system further comprises one or more organic solvents miscible with water.

15. The method of claim 1 wherein said carrier system further comprises one or more therapeutic agents, chelators, or pH regulators.

16. The method of claim 1 wherein said frangible seal closes a terminal opening in said hollow body, and further comprising the step of breaking said frangible seal.

* * * * *